(12) United States Patent
Holden

(10) Patent No.: US 7,465,942 B2
(45) Date of Patent: Dec. 16, 2008

(54) PLUNGERS AND DEVICES FOR STORING PLUMBING TOOLS

(75) Inventor: H. Lee Holden, Los Gatos, CA (US)

(73) Assignee: Smart Products and Inventions, Inc., Los Gatos, CA (US)

( * ) Notice: Subject to any disclaimer, the term of this patent is extended or adjusted under 35 U.S.C. 154(b) by 142 days.

(21) Appl. No.: 11/386,255

(22) Filed: Mar. 21, 2006

(65) Prior Publication Data

US 2006/0213791 A1 Sep. 28, 2006

Related U.S. Application Data

(60) Provisional application No. 60/664,102, filed on Mar. 22, 2005.

(51) Int. Cl.
*A61L 2/10* (2006.01)

(52) U.S. Cl. .......... 250/455.11; 422/24; 4/255.11; 206/349; 206/361; 312/206; 312/207

(58) Field of Classification Search .......... 250/455.11; 422/24; 4/255.11; 206/349, 361; 312/206, 312/207
See application file for complete search history.

(56) References Cited

U.S. PATENT DOCUMENTS

| | | | |
|---|---|---|---|
| 2,044,594 A | 6/1936 | Scholfield | |
| 2,697,842 A | 12/1954 | Meyer | |
| 3,934,280 A | 1/1976 | Tancredi | |
| 4,182,688 A | 1/1980 | Murtaugh | |
| 4,186,451 A | 2/1980 | Ruo | |
| 4,211,750 A | 7/1980 | Gillespie | |
| 4,238,860 A | 12/1980 | Dixon | |
| 4,458,368 A | 7/1984 | Webb | |
| 4,674,137 A | 6/1987 | Girse | |
| 4,733,414 A | 3/1988 | Wilkes | |
| 4,768,237 A | 9/1988 | Torti | |
| 4,847,923 A | 7/1989 | Huang | |
| 4,877,963 A * | 10/1989 | Min-Jenn | 240/455.11 |
| D315,269 S | 3/1991 | Brazis | |
| 5,040,679 A | 8/1991 | Rehmann | |
| 5,156,538 A | 10/1992 | Lee | |
| 5,199,114 A | 4/1993 | Christopher | |
| 5,353,422 A | 10/1994 | Kobayashi | |
| 5,353,442 A | 10/1994 | Rotter | |
| 5,456,356 A | 10/1995 | Kurzawa | |
| 5,522,094 A | 6/1996 | Balazs | |
| D383,935 S | 9/1997 | Zawalsky | |
| 5,706,528 A | 1/1998 | Broback | |
| 5,766,116 A | 6/1998 | Weissbuch | |
| 5,772,015 A * | 6/1998 | Musiel et al. | 206/209 |
| 5,836,322 A | 11/1998 | Borger et al. | |
| 5,860,170 A | 1/1999 | Witt | |
| 5,862,534 A | 1/1999 | Clay | |
| D404,951 S | 2/1999 | Zawalsky | |
| 5,924,566 A | 7/1999 | Gibbs | |
| 5,927,492 A | 7/1999 | Moore | |

(Continued)

*Primary Examiner*—Jack I Berman
(74) *Attorney, Agent, or Firm*—Levine Bagade Han LLP

(57) ABSTRACT

A plunger that operates by a piston to drive a purging flow at relatively high pressure is disclosed. The plunger includes features so that the exterior of the plunger remains in a dry and sanitary condition. An optional storage unit is also disclosed where the storage unit includes at least one UV element. Where the UV element decreases the amount of pathogens on the plumbing tool.

32 Claims, 13 Drawing Sheets

U.S. PATENT DOCUMENTS

Figure 1A:
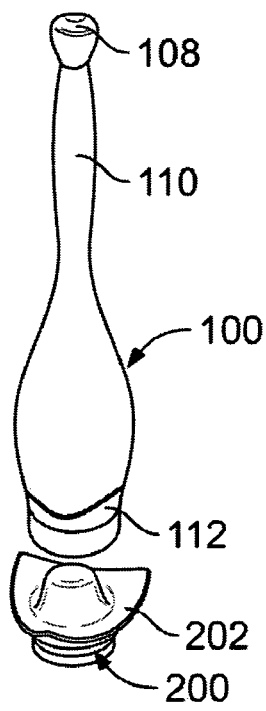

| | | |
|---|---|---|
| 5,940,897 A | 8/1999 | James |
| 5,958,150 A | 9/1999 | Borger et al. |
| 6,035,455 A | 3/2000 | Rankovic |
| 6,216,283 B1 | 4/2001 | Tash |
| 6,383,457 B1 | 5/2002 | Brown |
| 6,393,626 B1 | 5/2002 | Dhillon |
| 6,405,385 B1 | 6/2002 | Smith |
| 6,427,458 B1 | 8/2002 | Fowler |
| D463,698 S | 10/2002 | Phillips et al. |
| 6,487,730 B2 | 12/2002 | Pardo et al. |
| 6,510,860 B2 | 1/2003 | Kihs |
| 6,519,785 B1 | 2/2003 | Piercy, II |
| 6,524,529 B1 * | 2/2003 | Horton, III .................. 422/24 |
| 6,594,831 B1 | 7/2003 | Pardo et al. |
| RE38,291 E | 10/2003 | Kennedy et al. |
| 6,719,134 B2 | 4/2004 | Phillips et al. |
| 6,775,856 B2 | 8/2004 | Ollinger |
| 6,789,276 B2 | 9/2004 | Leaphart, Jr. |
| 2003/0017073 A1 * | 1/2003 | Eckhardt et al. .............. 422/24 |
| 2004/0025899 A1 | 2/2004 | Pinsky |
| 2004/0089815 A1 | 5/2004 | Woo |
| 2004/0159330 A1 * | 8/2004 | Anemone et al. .............. 134/1 |

\* cited by examiner

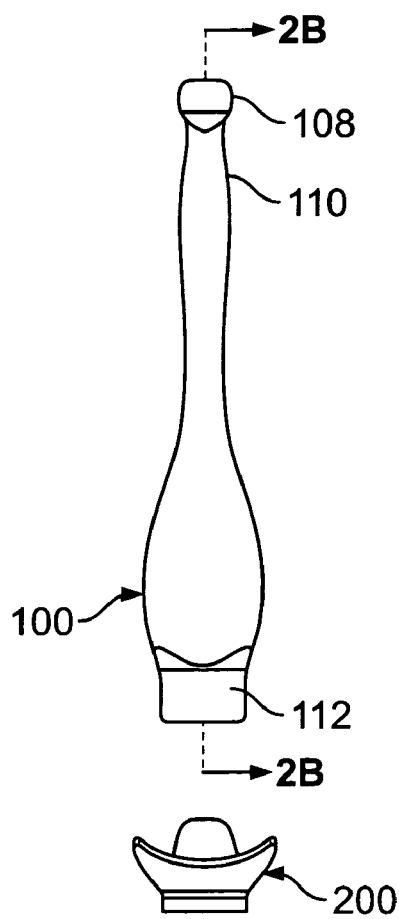
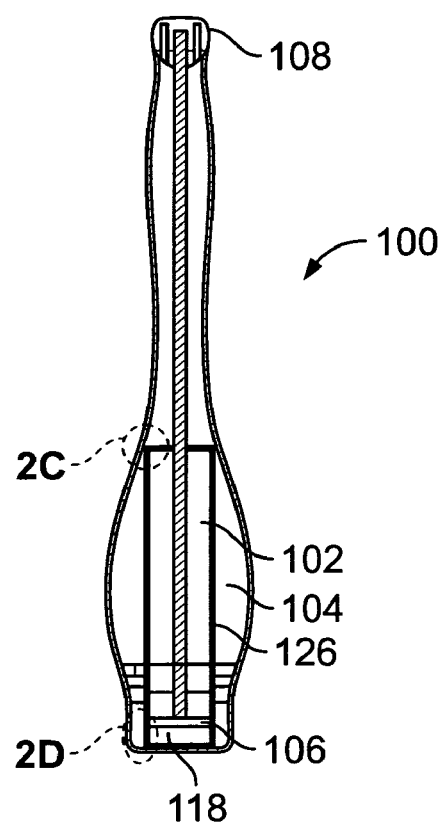
FIG. 2A
FIG. 2B
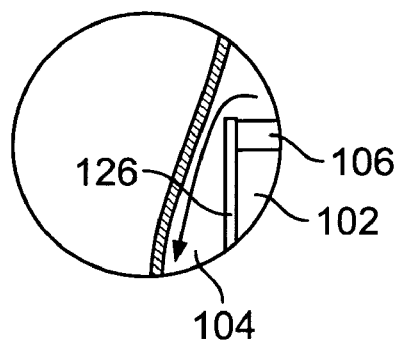
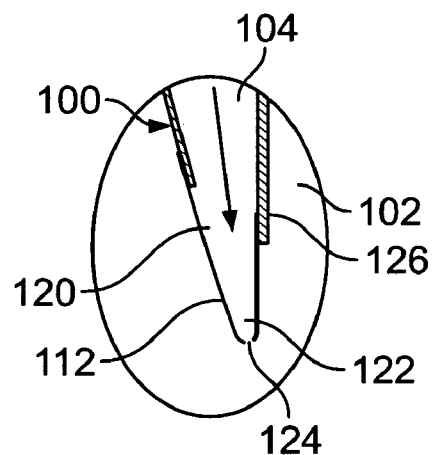
FIG. 2C
FIG. 2D

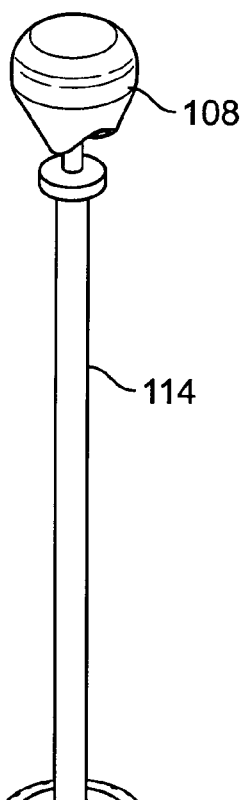
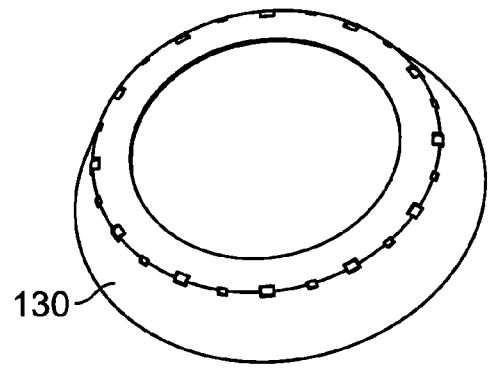
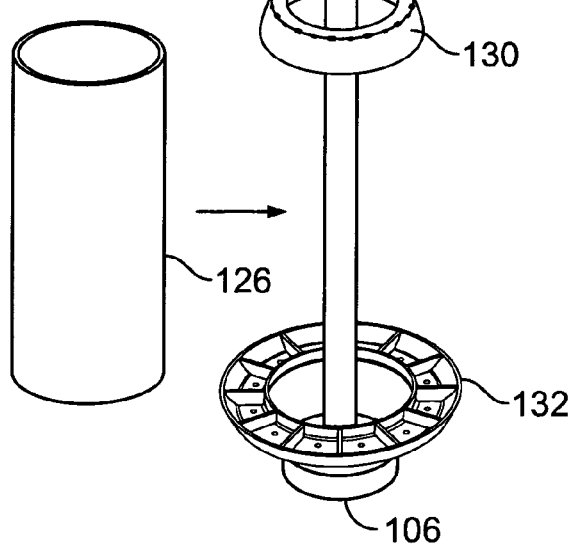
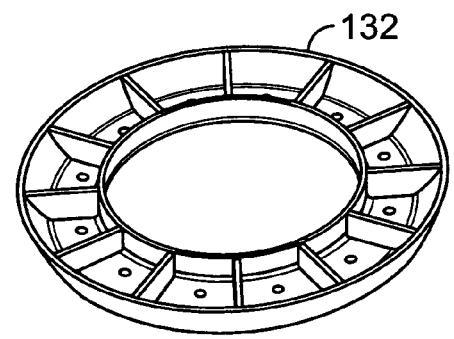
FIG. 4A  FIG. 4B  FIG. 4C

PLUNGERS AND DEVICES FOR STORING PLUMBING TOOLS

CROSS REFERENCE TO RELATED APPLICATIONS

This is a non-provisional of U.S. Patent No. 60/664,102 entitled PLUNGERS AND DEVICES FOR STERILIZING THE SAME, filed Mar. 22, 2005, the contents of which are incorporated in their entirety.

BACKGROUND OF THE INVENTION

A variety of tools have been developed for use in clearing an obstruction from a toilet, sink, and the like. For example, the most commonly used toilet plungers are relatively simple devices that are designed for non-professional plumbers. These simplistic plungers generally include a dome-like force cup with a rod attached thereto. The force cup is brought into contact with a drain outlet and pushed down by the rod to create pressure against the clog. While simple to use and relatively inexpensive, these types of toilet plungers have several drawbacks. Use of these plungers usually results in water and/or waste splashing out of the toilet to the surrounding area during use. In addition to requiring inconvenient additional clean-up, resulting contact of the toilet's contents with the user is unsanitary and may pose health risks. Furthermore, these common plungers often require a significant amount of physical effort by the user and often (either because of the user or design) are not effective.

Other devices utilize water pressure to dislodge toilet obstructions. For example, U.S. Pat. No. 4,768,237 discloses a toilet plunger having a conventional suction cup and handle. The handle of the device includes a connection for the supply of pressurized water deliverable to the clogged toilet outlet. U.S. Pat. No. 4,238,860 discloses a device that includes a pressurized water receiving-cup and a fitting to be secured within the outlet as water is passed therethrough. These water pressure devices are generally positioned in a sealing engagement with the outlet duct opening so as to rely on a general build up of pressure between the device and the obstruction to dislodge the obstruction. These devices also present a risk that water and other waste in the toilet bowl will splash on the user and surrounding area.

U.S. Pat. No. 2,697,842 discloses a combination hand and air force pressure pump and plunger. This device uses a complex arrangement of valves and conduits for causing a pressure differential at the drain clog. The plunger can be reversed on the base stem of the pump and a flexible hose extends therefrom. However, when used as hand plunger, the device is subject to many of the same disadvantages noted above, e.g., toilet contents such as water/waste contacting the user and using the force pressure mode requires a hook-up to an external pressurized air source. Furthermore, the device includes a piston having a felt or leather piston member making it unsuitable for contacting liquid to which it may be exposed. For example, felt or leather pistons do not easily dry-out, easily degrade upon water contact and may provide an environment for microbial growth.

Toilet plungers, toilet brushes, and similar cleaning devices are commonly known since little substantive change has taken place in this industry since the fist crude plungers and brushes arrived on the market. Furthermore, conventional products do not provide high-end toilet brushes and plungers that bring design, value and most importantly, sanitization to the bathroom. Pathogens (including bacteria and viruses) found in the bathroom (or other areas where plungers/brushes are used) cause serious health problems, and in extreme cases, can even cause death. Conventional methods for keeping these areas sanitized were limited to cleansing chemicals. Such chemicals pose a risk to occupants and also, ultimately, to the environment.

These conventional cleaning devices do not address health concerns, as they have no convenient sterilization capability. Often, storage of these products occurs in a damp, dark environment such as a container or the corner of the room. If contaminated, the brush, plunger, or other cleaning device becomes a breeding ground for viruses and bacteria and many other pathogens. Toddlers, children, pets, as well as adults, who come in contact with these plungers are exposed to the pathogens and risk becoming sick or carriers of the pathogens. The problem is exacerbated in public-use areas such as hospitals, restaurants, dormitories, hotels, and even nursing homes.

The introduction of products with disposable cleaning ends (such as disposable toilet brushes) is one attempt to address this sterilization and cleanliness issue. For example, SC Johnson's Scrubbing Bubbles Fresh Brush, Clorox's Toilet Wand and Scotch Brite's Disposable Scrubbers are products aimed at reducing contamination. However, aside from the increased cost burden, these products still require a non-disposable component (such as a shaft, handle, arm, body, etc.), that may serve as a breeding ground for such pathogens.

UV light sterilization is a safe and proven technology that is widely used in hospitals, air and water purification, food processing and packaging, medical packaging. UV light sterilization is also found in toothbrush holders and surface cleaning sterilizers.

Ultraviolet (UV) light is part of the light spectrum between 100 and 400 nanometers (nm), just below the violet end of the visible spectrum. UV technology is a non-chemical approach to disinfection. In this method of disinfection, no chemicals are added, which makes this process simple, inexpensive and low maintenance.

UV sterilizers use germicidal lamps designed and calculated to produce a certain dosage of ultraviolet light. The principle of design is based on a product of time and intensity. Both parameters require specified levels for successful disinfection.

Accordingly, there remains to be a need for improved plumbing related products.

SUMMARY OF THE INVENTION

The devices and methods described herein are improved means for handling and storing plumbing-related products, especially bathroom-related products and plumbing tools. The plumbing tools may include plungers, toilet brushes, handles for disposable toilet brushes/plungers, other types of plumbing accessories such as drain brushes, drain snakes, and other similar type cleaning or clearing implements.

One variation of a device provides for a cleaner plumbing tool that improves clears obstructions in a toilet or other drain in an improved manner. Another particular feature of the products and methods described herein is that they increase the ability of the user to maintain a clean device yet do so in a safe and effective manner lessening or even eliminating the need for chemicals.

It is specifically noted, that products and methods described herein increase the sanitization aspect of these plumbing related products and may also sterilize the products. With regards to sterilization, the products and methods herein may allow for total sterilization by eliminating the threat from harmful substances, or, the products and methods may partially sterilize the products by reducing the amount of harmful substances on the plumbing related devices.

The invention includes a plunger for clearing a drain, where the plunger has a plunger body comprising an upper body portion and a lower body portion, where the upper body portion includes a handle and a gripping section, a reservoir located within the plunger body and terminating at an opening in the lower body portion, where the opening is adapted to direct fluid into the drain, a piston slidably moveable in the reservoir, such that movement of the piston displaces fluid from a first reservoir portion to a second reservoir portion, where the second reservoir portion comprises at least one port in the lower body portion allowing liquid in the second reservoir portion to exit the plunger body at a location away from the upper body portion, and a compliant member located adjacent to the opening, where the compliant member is sufficiently compliant to form a seal between the lower body portion and the drain allowing fluid to be drawn into the first reservoir portion via the opening.

In another variation of the invention, a plunger can include a first chamber substantially surrounded by a housing and spaced-apart a distance from an interior surface of the housing, the chamber comprising a top end and a bottom end, the top end being substantially open, and a piston movably and sealingly arranged within the first chamber. A space between a wall of the first chamber and the interior surface of the housing can define a second chamber, and where the first and second chamber are in fluid communication only at a top of the first chamber, such that material flowing around the piston is forced into the second chamber.

The invention also includes a storage unit for sanitizing or sterilizing a plumbing tool, the unit can include a base adapted to sealingly hold the plumbing tool, and at least one UV light source within the base. Variations of the invention include storage units that sterilize/sanitize with our without rinse cycles.

The invention also includes methods for clearing obstructions from a toilet or drain by positioning a distal end of a plunger in a source of liquid; drawing liquid from the liquid source into the inner member (e.g., the reservoir); positioning the inner member over an outlet of a toilet and forming a seal against the drain; and forcing the liquid from the inner member into the outlet without undue splashing of the liquid found in the toilet. The method includes optionally cycling liquid with the plunger through the drain without breaking the seal. Eventually, the toilet drains when the seal is removed.

BRIEF DESCRIPTIONS OF THE DRAWINGS

Figure 1B:
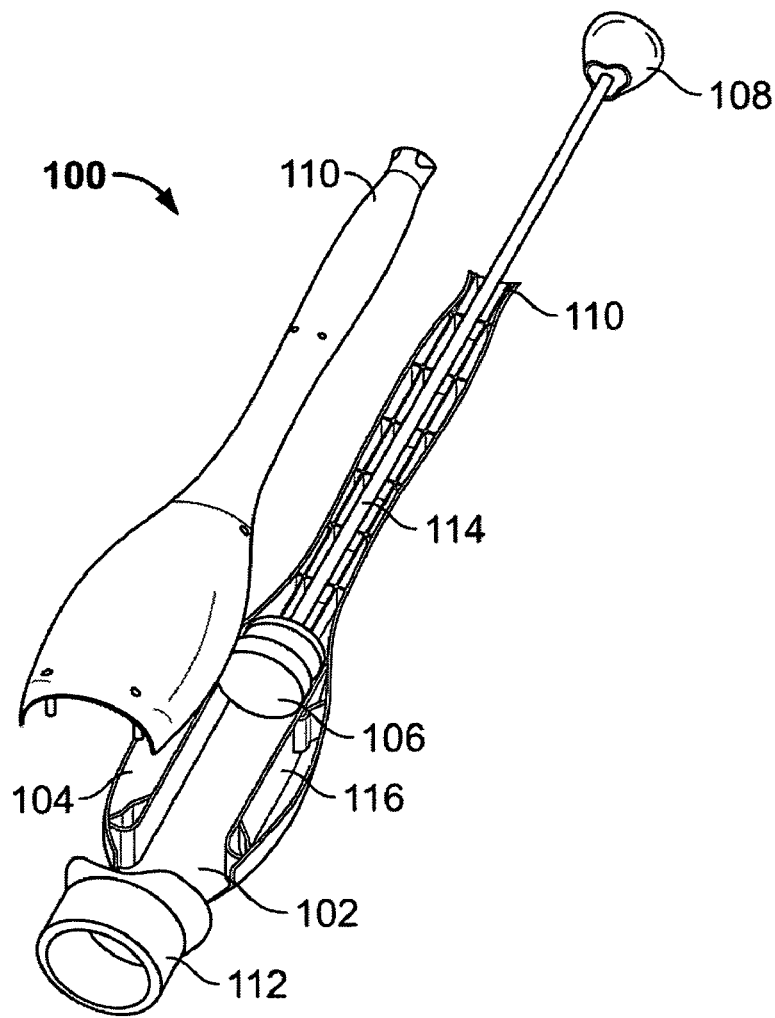
Figure 1C:
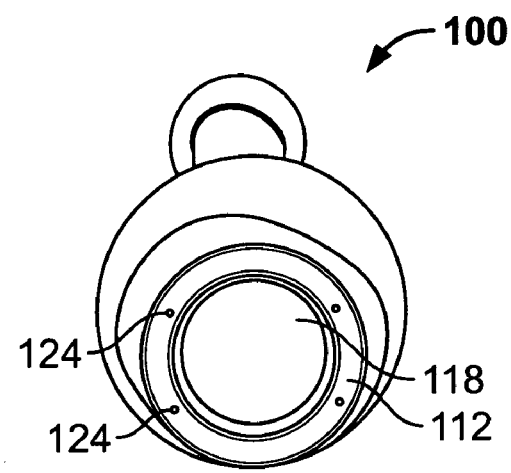
Figure 1D:
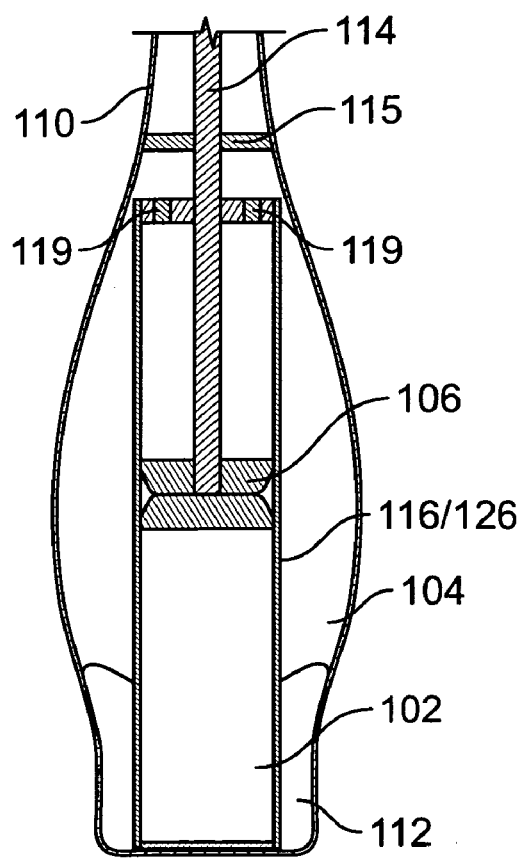
Figure 5C:
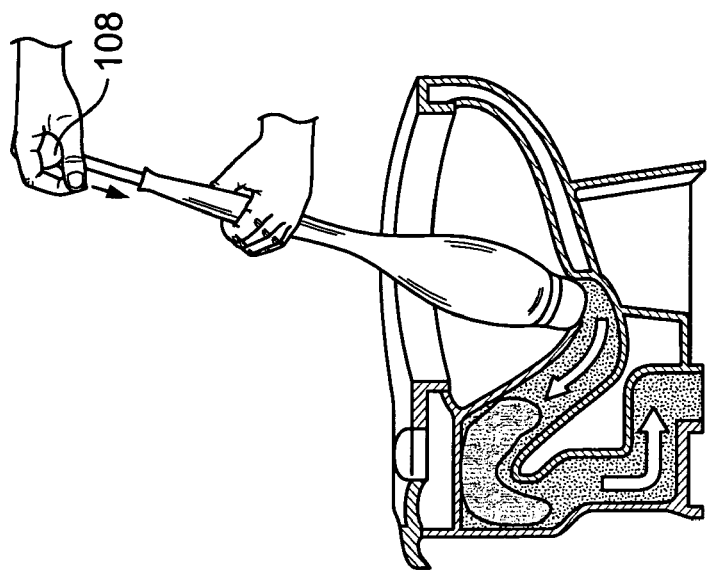
Figure 5B:
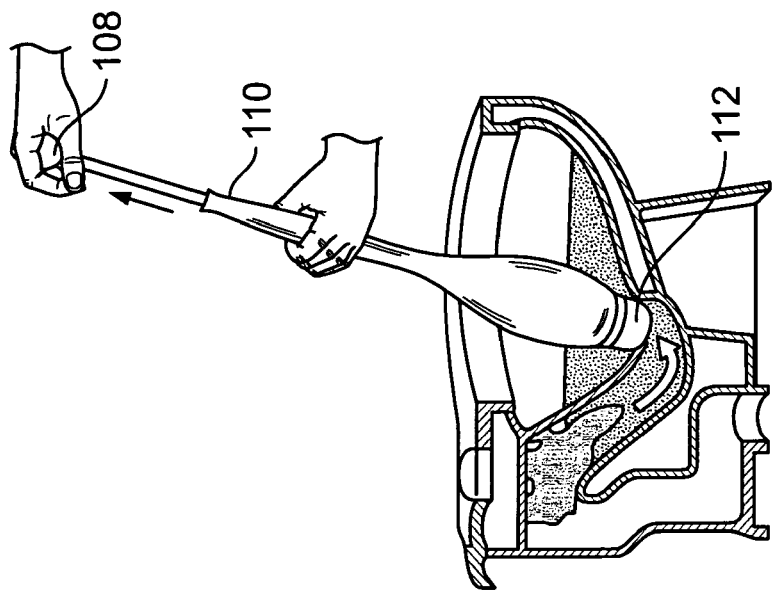
Figure 5A:
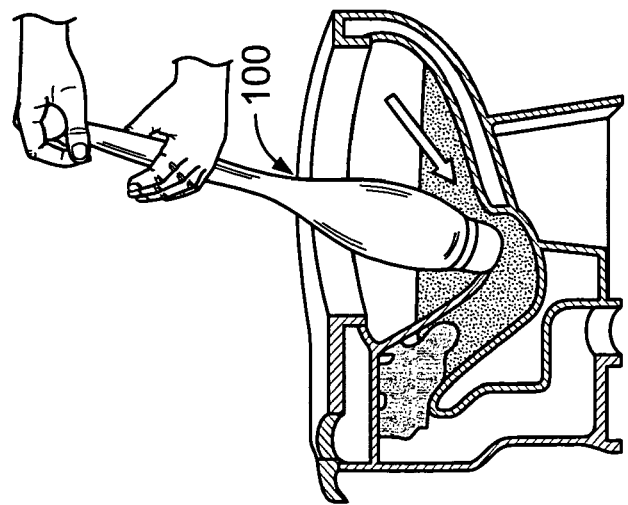
Figure 6A:
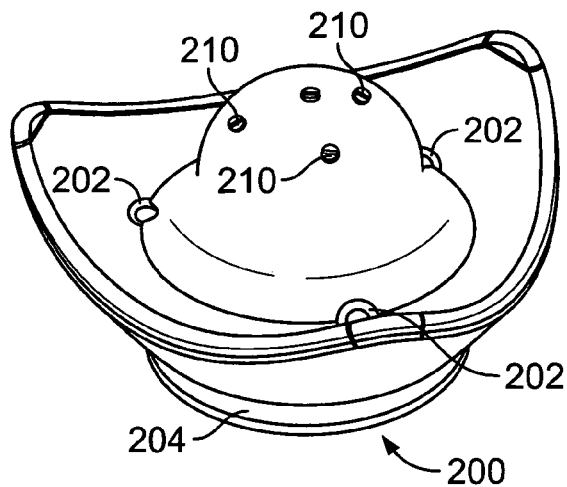
Figure 6B:
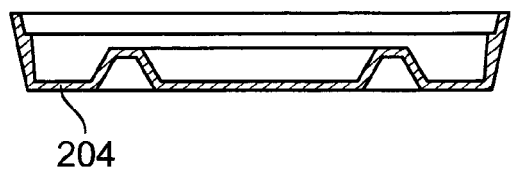
Figure 6C:
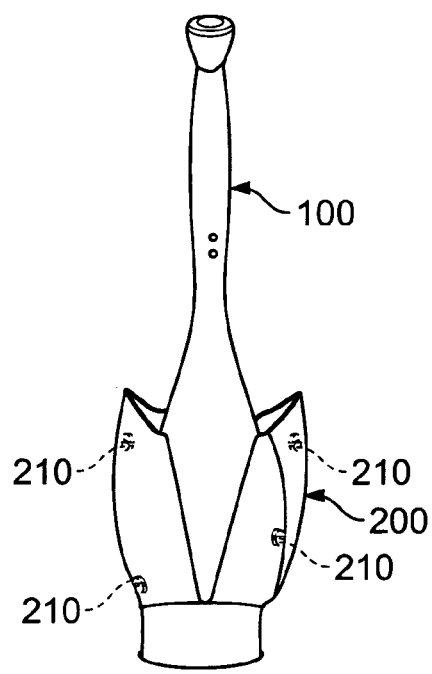
Figure 7A:
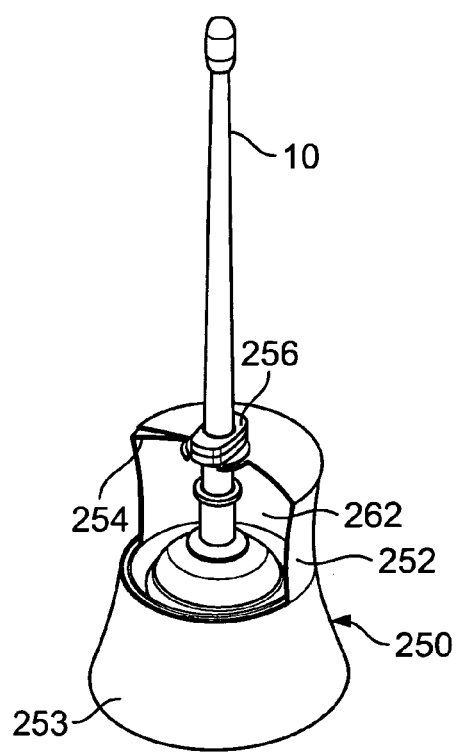
Figure 7B:
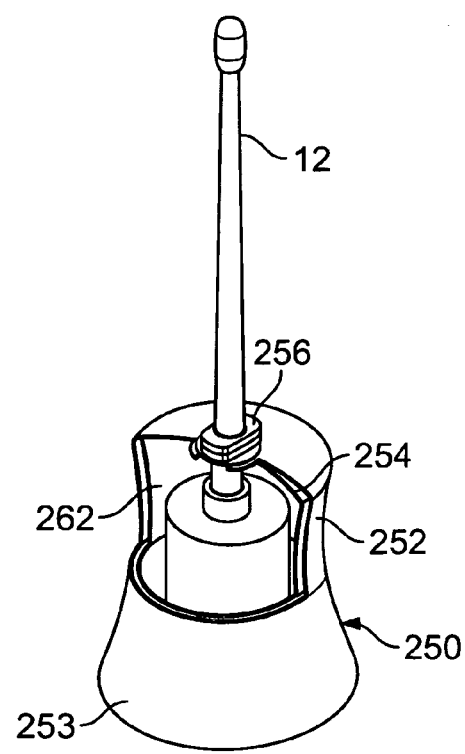
Figure 8A:
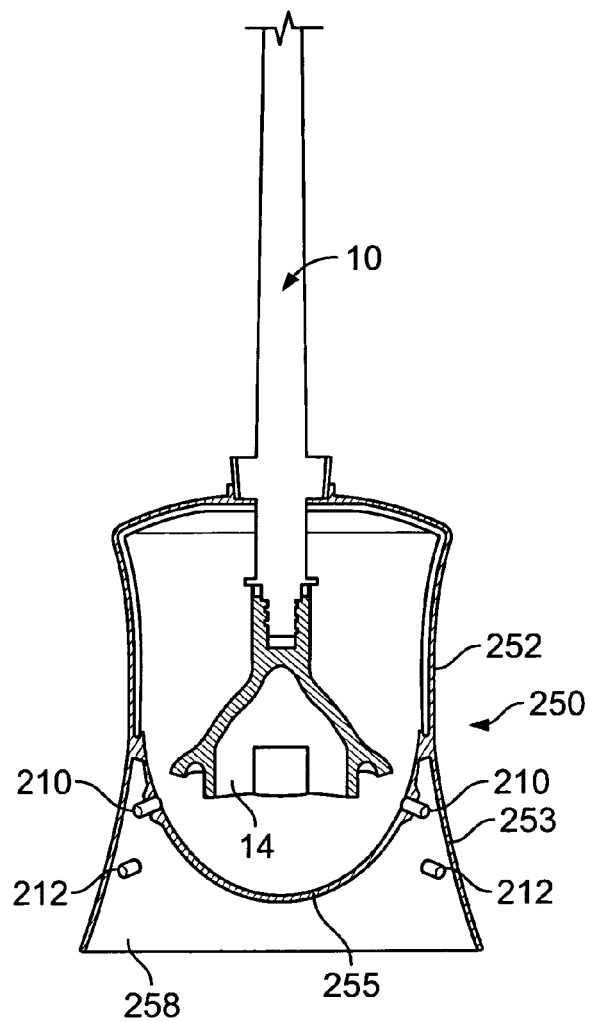
Figure 8B:
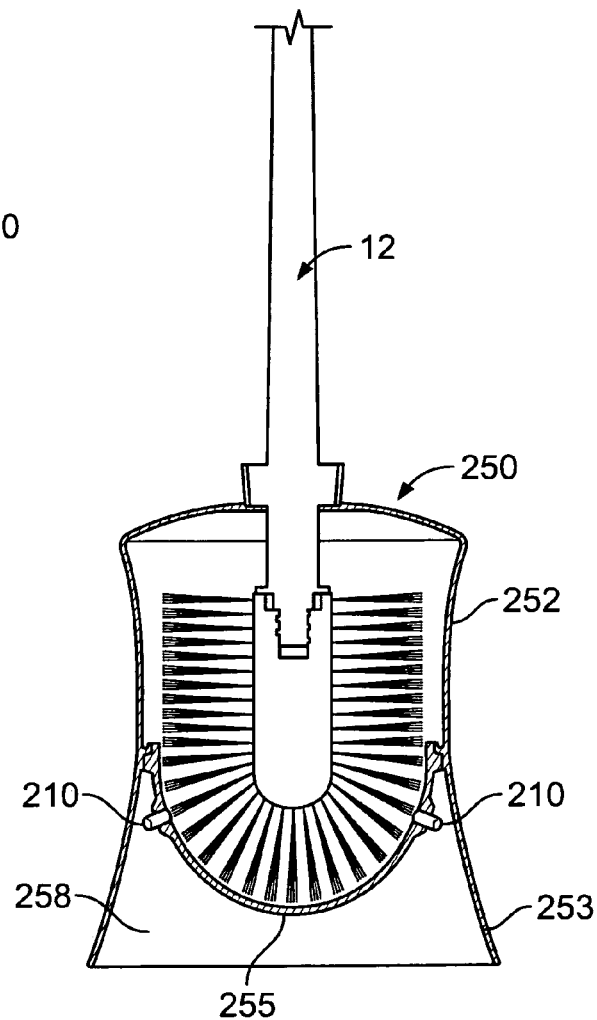
Figure 9A:
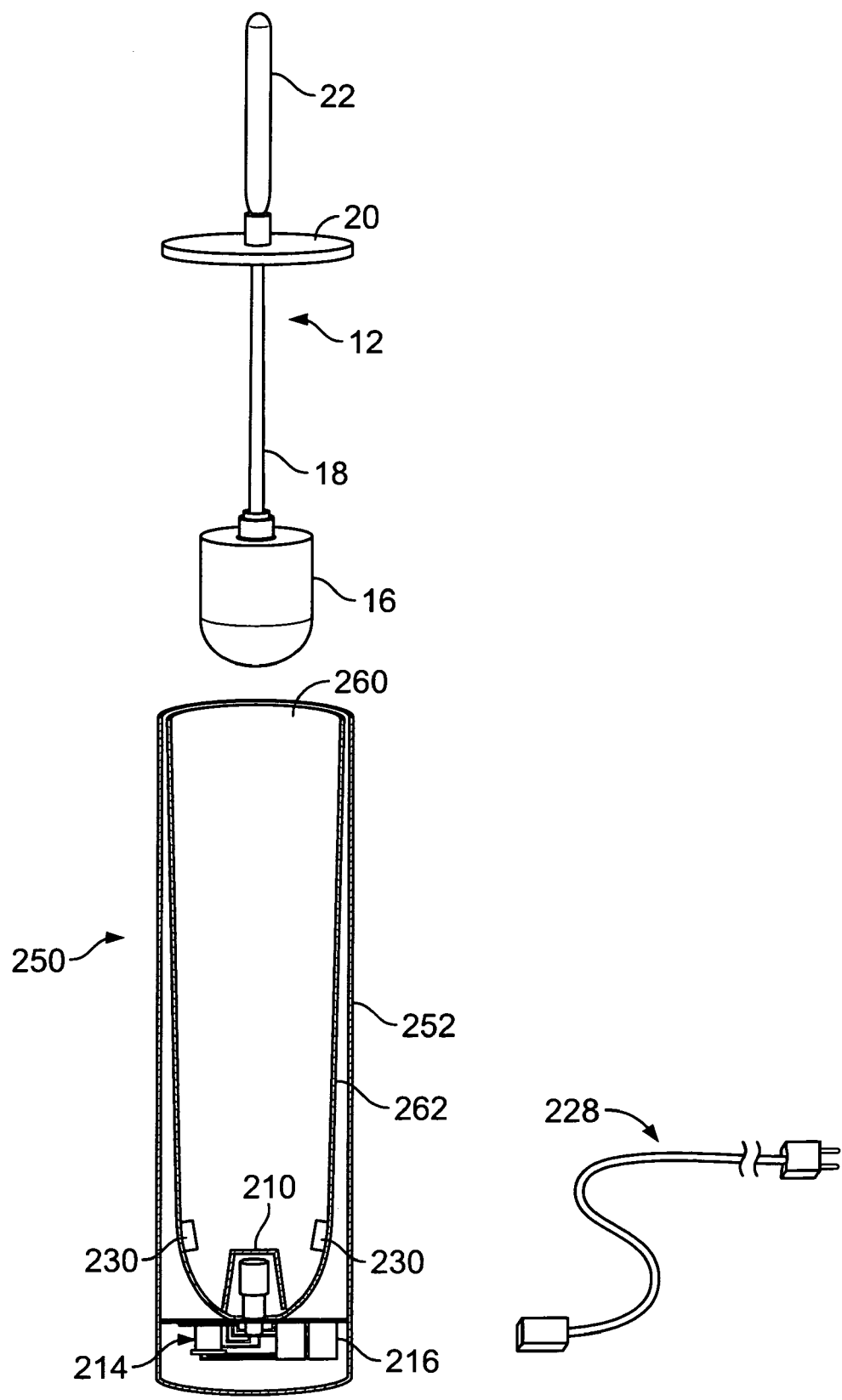
Figure 9B:
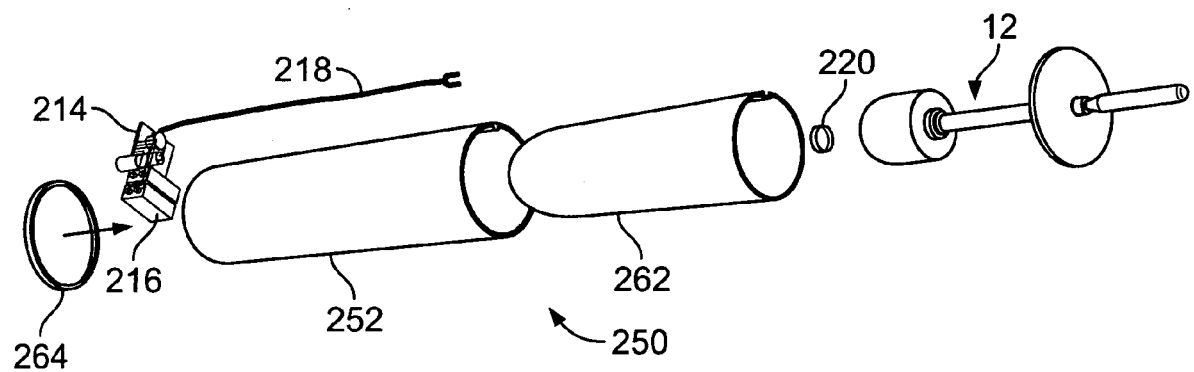
Figure 9C:
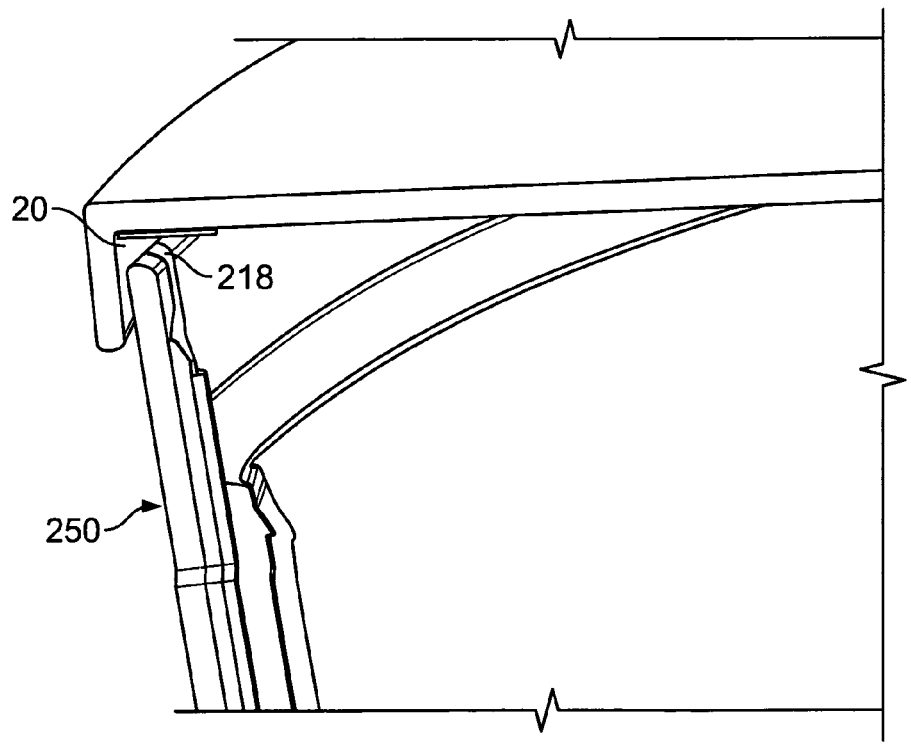
Figure 9D:
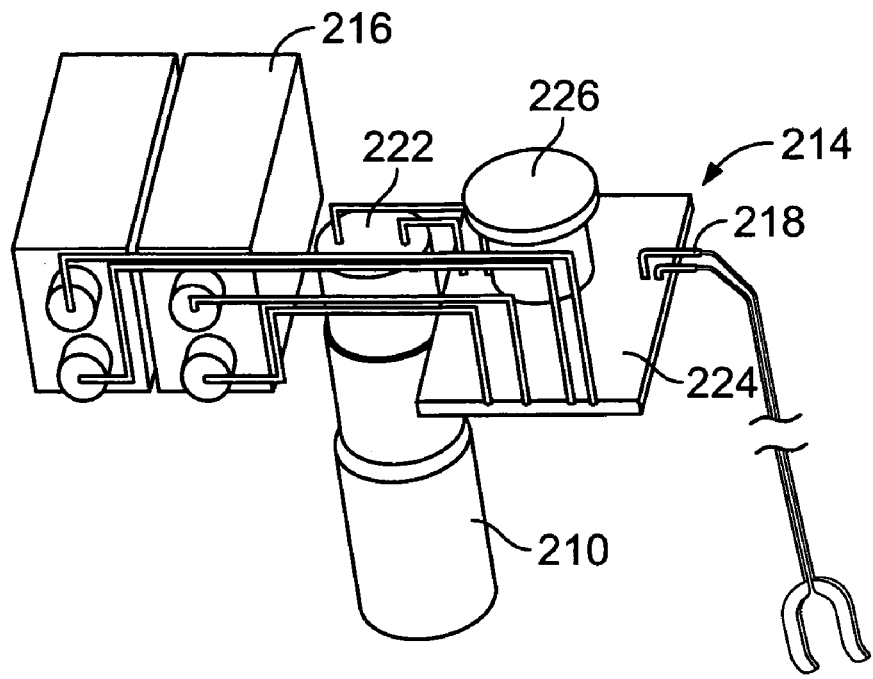
Figure 9E:
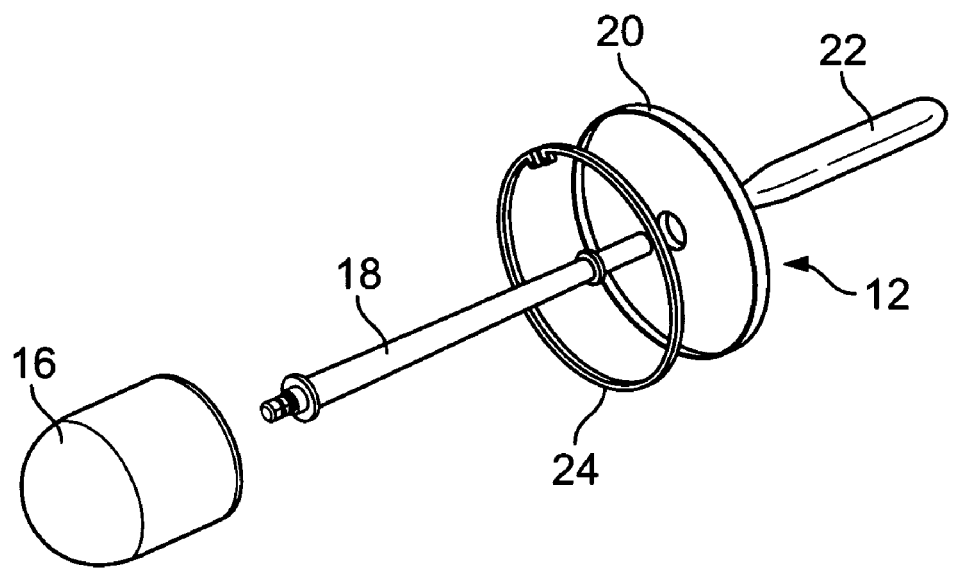
Figure 10:
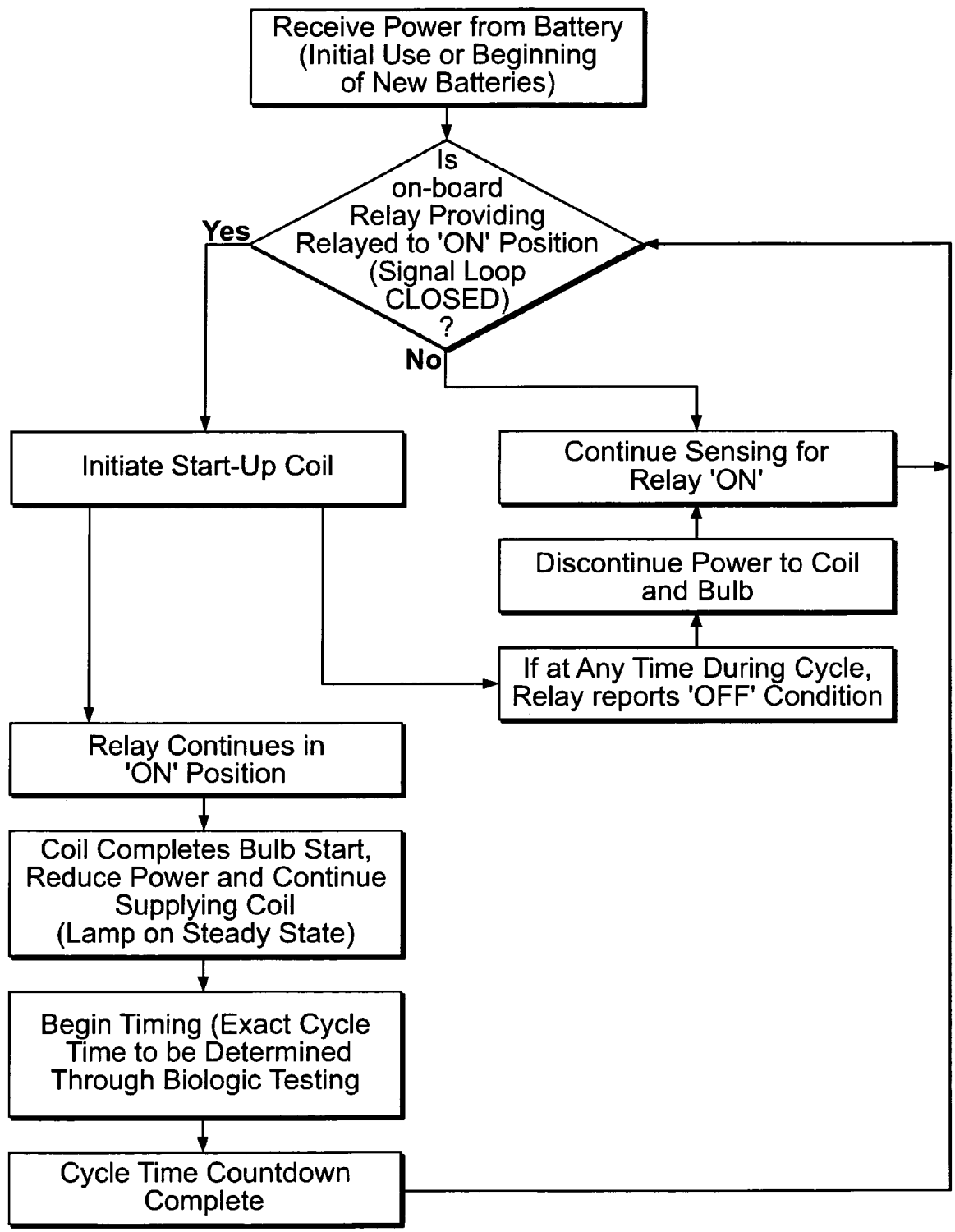

The figures illustrate exemplary aspects of the invention. Of these figures:

FIG. 1A is a view of an variation of a plunger and a base;
FIG. 1B is an exploded view of the plunger of FIG. 1A;
FIG. 1C is an end view of the plunger of FIG. 1A;
FIG. 1D is an partial section view of an end of a plunger;
FIG. 2A is another variation of a plunger;
FIG. 2B is a cross-sectional view of the plunger of FIG. 2A taken along lines A-A;
FIG. 2C shows an enlarged view of a portion of the plunger of FIG. 2B showing the flow-by path for liquid that gets behind the piston seal of the plunger; FIG. 2D shows an enlarged view of a portion of the plunger of FIG. 2C showing the final exit path of liquid that gets behind the piston seal of the plunger (i.e., flow-by liquid);
FIGS. 3A-3E illustrate various internal components of variations of plunger under the present invention;

FIGS. 4A-4C are perspective/assembly view showing a piston sleeve, plunger rod, upper and lower retaining rings and a piston of the plunger;
FIGS. 5A-5C illustrate a variation of the plunger being used to clear a drain/toilet;
FIGS. 6A-6C shows a view of a base and plunger;
FIGS. 7A-7B shows exemplary plunger/toilet brush storage units according to the present invention where the unit is opened for insertion of a plumbing tool;
FIGS. 8A-8B show partial sectional views of storage units with UV sources for use with plumbing tools;
FIG. 9A shows a cross sectional view of another variation of a unit with a side view of a plumbing tool;
FIG. 9B illustrates an exploded view of the unit of FIG. 9A;
FIG. 9C illustrates a partial sectional view of a lid of a plumbing tool as it engages a switch on a base unit;
FIG. 9D illustrates an exemplary UV lamp and power supply;
FIG. 9E illustrates an exploded view of a toilet brush; and
FIG. 10 illustrates a flowchart representation of a variation of the logic flowchart contained on a circuit board for controlling the unit.

DESCRIPTION

The subject invention provides devices and methods for clearing an obstruction from a drainage outlet ("outlet") of a toilet, sink, washbasin, shower, bath, urinal, and the like. Although variations of the devices described herein are discussed primarily for use in clearing an obstruction from a toilet, the devices and systems are not limited to such a use unless otherwise discussed. Although the subject plungers described herein work optimally with its seal engaged under submerged conditions, variations of the invention may not be required to function in this manner. Embodiments of the subject invention are described with reference to FIGS. 1-8C.

Generally, embodiments of the subject plunger are constructed to prevent contents of the toilet (water, waste, obstruction particulates, etc.), from contacting the exterior surface of the plunger when the plunger is used to dislodge or break-up an obstruction in a toilet, thereby preventing liquid from coming in contact with the user of the plunger—especially the user's hands when using the plunger.

FIG. 1A illustrates a variation of a plunger assembly 100 according to the present invention. As illustrated, the plunger assembly or device 100 includes a handle 108, a neck portion, and a compliant member 112. Typically the plunger 100 will comprise a handle 108 and a gripping section. In the variation of FIG. 1A, the gripping section may comprise a neck portion 110 such that the handle 108 and gripping portion are on the upper part of the plunger body. However, variations of the plunger 100 include a gripping portion that is found on a lower part of the plunger body.

The compliant member 112 is sufficiently compliable and/or conformable to permit formation of a seal between the plunger 100 and drain and/or toilet. A full or partial seal allows the plunger 100 to intake and exhaust fluids to clear any obstructions. The compliant member 112 for use with the devices described herein may be resiliently deformable members such as a soft, pliable double wall gasket such as an elastomeric gasket. The compliant member 112 can be conformable to the bottom or liquid dispensing end of the plunger and adapted to sealingly engage the opening of a the toilet outlet or drain. The gasket thus provides a flexible member that may form a seal against a variety of toilet bowl shapes and is adapted to allow a distal plunger location for flow-by liquid to discharge from the plunger (into the bowl during use or into the base if it has not fully drained when it is put away).

The gaskets may be double walled gaskets. As shown herein, the gasket may connect to the housing wall to form a double lap joint and to the sleeve wall to form a single lap joint, as well as being adapted to be permissive of liquid flow therethrough.

The gasket can include at least one through hole by which liquid (from within the chamber and/or from the flow-by path) is dispensed from the plunger to the drain. In certain embodiments, a gasket includes at least one liquid dispensing opening in communication with the interior of the sleeve and at least one liquid dispensing opening in communication with a flow-by path.

As noted above, in the variation of FIG. 1A, the upper portion of the plunger 100 comprises the handle 108 and neck portion 110. Where the neck portion 108 is convenient for the user to grip when using the plunger 100. Although not shown, variations of the invention include a handle 108 and/or neck portion 110 having a handle grip type configuration to allow for the user to apply greater force when using the plunger 100. The lower body portion generally includes the compliant member 112 and the part of the plunger 100 containing a reservoir (not shown in FIG. 1A). Again, variations of the plunger 100 include the gripping portion located on the lower body portion.

The system described herein may include base 200, where the lower body portion nests within the base 200 when not in use. As shown, the base 200 may include drain openings 202 to allow any liquids to drain from the plunger 100 when in storage.

FIG. 1B illustrates an exploded view of the plunger device 100. As shown, the piston 106 is slidably located within a reservoir portion or first chamber 102. The piston 106 is coupled to a shaft 114. The shaft 114 terminates in a handle 108. This configuration allows an operator to grasp the neck portion 110 and handle 108 to actuate the plunger device 100 while allowing the working end of the device 100 to direct fluid. As illustrated, the neck portion 110 may contain ribs to increase its column strength. Alternatively, the neck portion may be solid. Variations of the device 100 include at least two shells that form the body of the device 100. Alternatively, the plunger device 100 may be a single uniform piece of material. In any case, plugs may be used to fill any openings (caused by fastening members) in the external portion of the plunger body.

As discussed below, the internal surfaces of the plunger assembly 100 may be reflective such that UV light is reflected within the reservoir to assist in sterilizing the plunger. Alternatively, or in combination, a UV light source or other sterilization source, may be placed within the reservoir or housing of the plunger. In such cases, a power supply will be coupled to the plunger (either through a coupling in the base, a battery operated system in the plunger body, or an external plug or charging source. Furthermore, a photocatalyst may be provided with the plunger. For example, the photocatalyst may be provided in the material forming the plunger parts. Alternatively, or in combination, the photocatalyst may be provided as a separate insert that is placed within the plunger. In any case, the photocatalyst will be placed within a line-of-sight of the UV light source and/or it will be placed such that UV light shines onto and activates the catalyst.

FIG. 1B also shows the plunger 100 including a reservoir for displacement of fluids (where fluids include gas and liquids). The reservoir is generally divided into a first reservoir portion 102 or first chamber 102 and a second reservoir portion 104 or second chamber 104. The reservoir, usually the first reservoir portion 102 terminates at an opening 118 in the lower body portion, where the opening is adapted to direct fluid into the drain. The piston 106 is slidably moveable in the reservoir, such that movement of the piston displaces fluid from the first reservoir portion 102 to the second reservoir portion 104. The second reservoir portion 104 comprises at least one port 120 in the lower body portion allowing liquid in the second reservoir portion 104 to exit the plunger 100 body at a location away from the upper body portion. This assists in preventing fluid wastes from the plunger 100 from contacting the user's hands.

In the variation of FIG. 1B, the first and second reservoir portions 102, 104 are separated by a wall 116. The wall 116 spaces the first reservoir portion 102 from the body of the plunger. The spacing may then form the second reservoir portion 104. To permit fluid flow between the reservoir portions, the wall can be open at the top of the reservoir portions 102, 104 to allow for fluids to be displaced between reservoir portions 102, 104. For example, when the piston moves from the bottom of the plunger to the top of the first reservoir portion, air in the first reservoir portion displaces into the second reservoir portion. It is noted that any liquid may also move to the second reservoir portion without contacting the user or exterior of the plunger. As the piston moves upward in the plunger body, liquids fill in the first reservoir portion through the opening 118 in the bottom of the plunger. This fluid path between reservoir portions 102, 104 is referred to as a "flow-by path". It should be noted that the wall may have other openings as well as openings in the top.

FIG. 1C illustrates a view of the bottom of the plunger 100. As shown, the opening 118 of the reservoir is adjacent to the compliant member 112. Some variations of the device 100 may include a compliant member 112 having a cavity 122 (not shown). In such cases, the cavity 122 will have cavity openings 124 or apertures 124 to allow fluid to drain from the plunger through the port 120 of the reservoir. Variations of the device 100 include ports that deliver fluid to an external surface of a lower body portion of the plunger or even back into the reservoir.

FIG. 1D illustrates a partial sectional view of the plunger 100 of FIGS. 1A-1B. As shown, the piston 106 is slidably moveable within the first reservoir portion 102. The shaft 114 passes through the reservoir and into the neck portion 110. To prevent liquids form entering the neck portion 110, a shaft opening 115 into the neck portion 110 may have a close tolerance to the shaft 114 and/or a seal may be used. In addition, to allow fluid communication between reservoir portions 102, 104, one or more flow-by openings 119 may be used. For example, if the plunger 100 uses a wall 116 to separate reservoir portions 102, 104, then the wall may have openings 119 as shown. Alternatively, if the first reservoir portion 102 is defined by a sleeve 126, then the sleeve may have openings 119 or may have an insert or cap with such openings 119.

FIG. 2A illustrates another variation of a plunger 100 according to principles described herein.

FIG. 2B shows a cross sectional view taken along the lines A-A of FIG. 2A. As shown, the plunger 100 includes a sleeve 126 defining a first reservoir portion 102 or first chamber 102. Where, a piston head 106 is moveable in the first chamber 102 and serves as the mechanism to draw fluid in the assembly 100 and generate hydraulic pressure to unclog a drain such as a toilet drain or the like.

As shown in FIG. 2B, the second reservoir portion 104 or second chamber 104 is exterior to the first reservoir portion 102 or first chamber 102. As discussed above, the sleeve 126 is open at the top to allow for a flow-by path between chambers. This permits confinement of liquid within plunger device.

FIG. 2C is an expanded view of the balloon 2C from FIG. 2B. As shown, the double wall construction formed by the sleeve 126 helps confine liquid that may pass behind the piston 106. This fluid is referred to as "flow-by liquid". The flow-by liquid then exits the device 100 in a direction away from the user/handle 108.

FIG. 2D is an expanded view of the balloon 2D from FIG. 2B. As shown, the port 120 from the second chamber 104 permits flow-by liquid to enter into a cavity 122 of the compliant member or gasket 112. The flow-by liquid then exits via the aperture 124. In this manner, the component pieces of the plunger 100 direct liquid to exit the plunger (e.g., to return to the toilet, or drain into the base 200) without contacting the exterior surface of the plunger. As noted above, variations of devices includes aperture and/or ports that deliver flow-by liquid externally to the body of the plunger in the lower body portion.

Figure 3A:
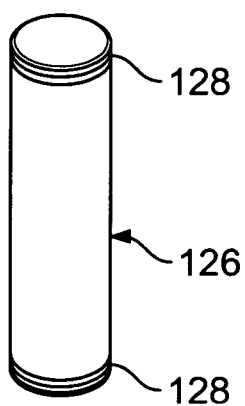

FIGS. 3A-3E illustrate various internal components of the plunger 100. FIG. 3A illustrates a variation of a sleeve 126 for use with a plunger 100. As shown, the sleeve 126 includes mating portion 128. The mating portions may be threaded portions, have ridges, or other such features that allow for placement and securing of the sleeve within the plunger body and (optionally) to the compliant member or gasket. Typically, the bottom end of the sleeve allows for liquid to pass into and out of the plunger. The top end of the sleeve may be adapted to provide substantially unobstructed flow for flow-by liquid to the flow-by path. The top end of the sleeve may be substantially, including completely, open, thereby accommodating a wide volume of liquid that may leak past the piston/sleeve seal during use of the plunger.

Figure 3B:
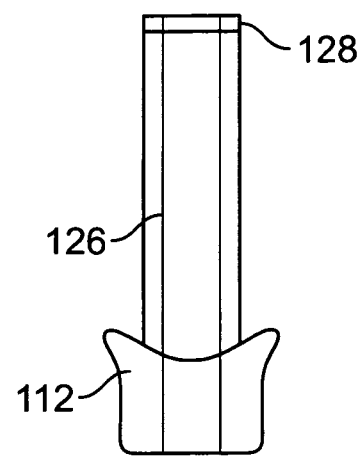
Figure 3C:
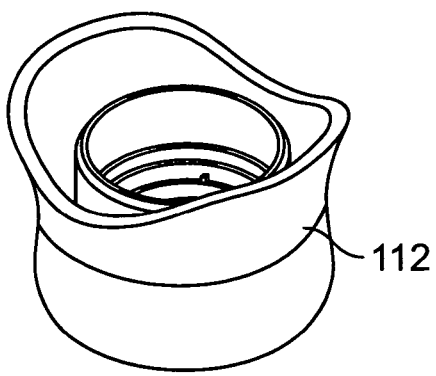
Figure 3D:
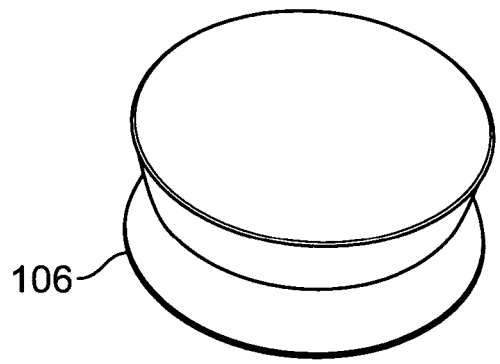

FIG. 3B illustrates a sleeve 126 being joined to a gasket 112. FIG. 3C illustrates a gasket 112 or compliant member 112. The gasket may be comprised of a thermoplastic elastomer. As noted herein, the materials used for the gasket are capable of cyanoacrylates and epoxies. The materials should be useful for industrial applications and should b compatible with heavy alkalis. FIG. 3D shows a variation of a piston 106. The piston 106 may be fabricated from a thermoplastic elastomer, thermoplastic rubber/resin, polypropylene or any similar material. As shown, the piston may have a double seal and a flat top. Both 'ridgelines' or seals on on the piston may form an independent seal with the sleeve. Finally, the top of the piston should not have cavities or wells in which 'flow-by' liquid may collect. However, other configurations of pistons may also be employed.

Figure 3E:
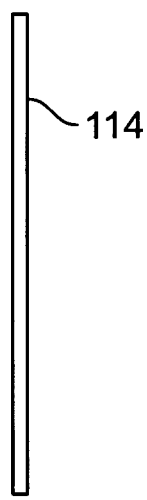

FIG. 3E illustrates a shaft 114. The shaft 114 may be fabricated from a stiff material such as a steel coated with a corrosion inhibiting material. Alternatively, the shaft may be fabricated from a stiff polymer.

FIG. 4A-4C illustrates another variation of a set of internal components. FIG. 4A shows a sleeve 126 that is positioned in the interior of the housing and maintained in a fixed position by one or more sleeve-holding members or fixtures 130, 132 which may be in the form of rings (e.g., rings with perforations to maintain the flow-by path allowing for passage of flow-by liquid). For example, an upper retaining ring and/or a lower retaining ring may be used.

The sleeve 126 may be spaced a distance apart from the housing so that spacing between the outer surface of the sleeve and the inner surface of the housing is provided that defines a liquid flow-by path for flow-by liquid. Alternatively or in addition, the sleeve may include external grooves or flow channels for flow-by liquid. In one variation, the sleeve outer housing and flow channels may provide an integrated or one-piece structure.

In any case, spacing between the first reservoir portion 102 (i.e., the piston bore) and housing defines the second reservoir portion 104 and provides a liquid flow path that is adapted to receive flow-by liquid and direct the flow-by liquid to the bottom or dispensing end of the plunger. The flow-by path terminates at the distal or bottom end of the plunger or another location distal a user's grip position for return of flow-by liquid to the toilet bowl without user contact.

The sleeve 126 with the piston therein provides a chamber suitably constructed for receiving and holding liquid, until the liquid dispenses from the reservoir (or chambers) through an outlet to a toilet, by actuation of the piston. The chamber is designed to be compatible with substantial liquid contact. In other words, the chamber is constructed so that it is robust for repeated contact with liquid (e.g., toilet water, waste, etc.), and does not provide an environment for fostering microbial growth that may result from contact with contaminated toilet water.

The sleeve 126 is typically substantially rigid and constructed to maintain rigidity upon repeated and prolonged liquid contact. The sleeve 126 will typically be constructed of material that is compatible with drain-cleaning liquids, e.g., heavy alkali drain cleaners. A smooth bore is preferred, so seams should be avoided. Generally, extruded, pulltruded or cast polymeric material will suffice. Material of interest include, but are not limited to, polypropylene, poly(vinyl chloride), and other opaque, stiff, non-hydrophillic or hydrophobic thermoplastics, preferably one that is capable of adhesion with epoxies and cyanoacrylates. However, some choice of materials may be preferable for ease of manufacturing but such materials may not hold up to the heavy alkali drain cleaner discussed above. Materials include PVC, polypropylene or other such materials.

The piston typically includes a polymeric material. The piston may be a simple disc or be otherwise suitably configured. The type of seal required must be one such that the user can easily actuate the rod or handle attached to the seal. Consequently, the seal may not be air or liquid tight. Yet, it will generally only "leak" or allow about 0.001% to about 2% of the liquid it is driving past its face to pass. Still, either a better or worse seal may be employed.

The chamber is configured to hold and dispense a suitable volume of liquid for the various applications. For example, when intended for use to unclog a toilet, the chamber may have a liquid volume capacity (i.e., the volume of liquid that may be displaced by one stroke) that ranges from about 0.25 to about 2 liters, e.g., 0.5 to about 1.0 liters. In certain embodiments, the volume of liquid that may be displaced by one stroke may be as little as about 0.05 liters, e.g., if a motor is employed as described below.

Variations of the device include plungers with housings that include the sleeve-retaining portions and an elongate neck portion, wherein the two may differ in shape and/or size. For example, a sleeve-retaining portion may be in the form of a curved body portion (e.g., a bulbous portion), which curved body portion extends into a narrower neck portion that terminates in an opening. Such features may offer both design appeal as well as improved ergonomics.

The neck portion of the housing may be adapted to accommodate a shaft connected to the piston. The piston shaft may terminate in a user-contactable handle or knob which may protrude from the opening of the neck portion of the housing. The handle and/or neck may be configured to provide an ergonomic holding and controlling location for the operator of the plunger. An operator may hold the handle and move it upward and downward to drive the piston inside the sleeve in a reciprocating manner causing liquid to be dispensed from the plunger to the toilet outlet.

Variations of the device may include motor means disposed in the housing for driving the piston assembly in reciprocating motion. The motor may be actuated by a manual switch secured to the housing.

In another variation of the plunger, a system is provided that includes a brush portion (not shown) to be received at the bottom end of the plunger such that a subject plunger may be configured as a toilet brush. Alternatively, the body of the plunger may be adapted to accommodate either one of the seal or brush in an interchangeable fashion.

When no brush is attached to the plunger body, it may be received by a base. The base may include a central protuberance to help capture or stabilize the plunger received thereon. Adjacent this section, drain holes may be provided to allow fluid that remains in the plunger body to eventually leak out to accumulate in a reservoir base. Such a reservoir can be threaded onto or into an upper portion of the base. A chamber provided by these various components may be sized to receive a toilet puck, wafer or disk to aid in odor control.

Methods according to the invention include loading a plunger with liquid to be used to hydraulically clear an obstruction. However, FIGS. 5A-5C illustrate an example of use of a plunger 100 to clear a toilet. In using a subject plunger, downward hydraulic pressure may be repeatedly applied on an obstruction to dislodge or break-up the obstruction without contacting the exterior of the plunger with any liquid that bypasses the piston/sleeve seal of the device. Use generally includes two successive plunger strokes—a liquid pickup or loading stroke, followed by a liquid dispensing stroke. This cycle may be repeated a number of times to address the issue at hand As shown in FIG. 5A, the user positions a bottom end of the plunger 100 into a drain (in this case the toilet). Next, the compliant member 112 forms a seal between the body of the plunger 100 and the drain. Alternatively, the bottom end of the plunger is simply placed within liquid and water is drawn into the reservoir and then the end of the plunger forms a seal with the drain.

FIG. 5B shows a pulling motion on the handle 108 while the operator's hand holds the neck portion. This action draws liquid into the sleeve by causing the piston to move in a proximal direction within the reservoir. (i.e., away from the drain outlet).

Once loaded, the liquid may then be dispensed from the plunger with force. FIG. 5C illustrates a downward motion on the handle 108. Generally, the handle is pulled back and forth, causing the piston to move within the sleeve to force one or more streams of liquid from the sleeve and into the drain to dislodge and/or break-up an obstruction. This action may be repeated one or more times as needed. In certain embodiments, between about 2 and about 10 successive strokes may be used.

As discussed above, the use of the structure described above (including sealing the plunger, and the flow-by paths) prevents liquid from splashing or otherwise contacting the user's hands. Furthermore, the device only permits liquid to exit the device towards the bottom portion to avoid contacting the user.

FIG. 6A illustrates an example of a base 200 for use with plungers of the present invention. As shown, the base 200 may optionally include one or more drain holes 202 to drain liquids that accumulate after use of the plunger. FIG. 6A also illustrates one or more optional UV light sources 210 or other sterilization source. The base 200 may also include a base trap 204 used to collect any liquids that collect during storage of a plunger. FIG. 6B illustrates a cross sectional view of one example of a base trap. Variations of the invention may include bases with or without base traps.

FIG. 6C illustrates another example of a base 200 use with plungers 100 of the present invention. As shown, the base 200 may include one or more UV illumination sources 210 as discussed below. The UV sources 210 will be placed to sanitize/sterilize portions of the plunger 100 that come in contact with waste water from the drain/toilet.

The subject invention also provides ultraviolet (UV) sterilization units or base modules for use with plungers and toilet brushes. Accordingly, a subject UV sterilization unit may be used to sterilize or sanitize a plunger as described above (configured with a fluid gasket or with a brush), or any conventional plunger, toilet brush, and the like. The UV sterilization units may be used to aseptically store such a device for a prolonged period of time. Also provided are systems that include a sterilization unit and at least one of a plunger (including but not limited to a plunger of the subject invention) and a toilet brush.

Ultraviolet light is part of the light spectrum between 100 and 400 nanometers (nm), just below the violet end of the visible spectrum. Within UVC, wavelengths from 200 nm to 280 nm are known as the "germicidal range". Specifically, 253.7 nm is generally accepted as the apex of this range. Germicidal ultraviolet (UVC) light kills cells by damaging their DNA. The light initiates a reaction between two molecules of thymine, one of the bases that make up DNA. UV light at this wavelength (UVC) causes adjacent thymine molecules on DNA to dimerize. The resulting thymine dimer is very stable. If enough of these defects accumulate on a microorganism's DNA its replication is inhibited, thereby rendering it harmless.

The principle of design is based on a product of time and intensity—both levels must be specified for a successful sterilization. In one variation, the system delivers between 2,500-250,000 mWs/cm2 throughout the enclosure. This expose is believed to eliminate 95% to 99.9% of e. coli., Staphylococci, Streptococcus, Influenza, Hepatitis and many other pathogens. In additional variations of the invention, the container will be enclosed to protect the user from even the smallest dosage level of this light. Alternatively, or in combination, the system may include trigger switching to prevent unintended discharge of the UV light.

UVC light may be provided by fluorescent or low pressure-type bulbs. However, a more desirable source may be LED type bulbs which can produces ultraviolet light as well as Cold Cathode Fluorescent Lamps, which are smaller than the old Low Pressure bulbs. In one variation, the bulbs used deliver 95% of their energy as 253.7 nm. Systems of the present invention may be powered either from standard household electrical supply (e.g., 120 VAC). Alternatively, the system may be configured to use standard DC batteries such as AA, AAA, 9V or even watch batteries. In yet another variation, a wind-up dynamo (such as those used to power flashlights or radios) may be employed. Variations of the invention include devices used with any variation of the UV spectrum including UV cycles that provide varying ranges or wavelengths of the UV spectrum.

FIGS. 7A-7B illustrates variations of storage units as described herein. The storage unit 250 includes a base 252 where the bottom portion of the base comprises a skirt 253, having a UV source (not shown in FIG. 7A or 7B). This variation includes a gate 254 that is moveable to allow insertion and removal of the plumbing tool 10, 12. Typically, the gate 10 will be coupled to a switch for the UV source to avoid unintended exposure to the UV energy. The base can contain or surround a plumbing tool. Typically at least the distal end or head of the plumbing tool is located within the base. In additional variations, as much of the handle as is practical (i.e., a wetted or otherwise contaminated portion) is also enclosed in the base. The internal surface 262 of the unit 250 may have reflective properties to better distribute the UV energy. Optionally, the system or unit 250 may include a removable collar 256 that allows retention of a standard plumbing tool 10, 12 with the unit 250. However, in most variations, the collar 256 is not removable but integral with the tool. In some cases, a plumbing tool may be provided with the system, where the plumbing tool incorporates features to allow nesting of the tool within the unit.

FIGS. 8A and 8B illustrate cross sectional views of storage units 250. In these variations, the base 252 comprises an internal reflective surface at least in the area housing the plumbing tool 10, 12. Variations of the unit 250 includes the bottom portion of the base 252 As shown by the arrows, light from the UV light sources 210 bounces within the unit 250. Any number of UV light sources may be employed in variations of the devices. Moreover, the unit may be reflectively coated, or, the unit 250 may contain an insert that has a reflective coating. In variations of the unit 250 water that accumulates in a mid-wall 255 of the base 252 and eventually evaporates because of the UV exposure. In such variations, the base 252 is not in fluid communication with the interior skirt portion 258 of the unit 250 because the interior skirt portion 258 houses the electrical components and/or power supply of the system. Accordingly, the base 252 is sealed from the interior skirt portion 258 to prevent water seeping into the interior skirt portion. Typically, a mid-wall 255 separates the interior of the base 252 from the interior of the skirt 258.

In some variations, the interior portion of the skirt 258 may serve as a fluid trap 258 (e.g., the mid-wall 255 contains holes for drainage from the base 252 into the interior skirt portion 258). The fluid trap 258 collects liquid drainage from the plumbing tool. Optionally, the fluid trap 258 area may have a reflective coating to expose the fluid to UV light. Such exposure may be intended to reduce the pathogens in the drained fluid or to evaporate the drained fluid. In another variation, the fluid trap 258 may include a secondary source of UV light 212.

UV sources for use with the present invention include the following:

UV-A targeted at just below 380 nm in conjunction with a photocatalyst (e.g., TiO2). This could be performed with an inexpensive cold cathode glass bulb or an LED. Available UV-A LED's include: Roithner Lasertechnik # RLT350-30- peak wavelength of 350 nm, Roithner Lasertechnik # 380D30-380 nm, Roithner Lasertechnik # HUUV-5102L- 393-395 nm, LEDTronics # L200CUV395-12D-395 nm, Wilycon # WUV503-C395-C-390 nm minimum, 395 nm typical, 400 nm max, Nichia America, NSHU550E-370 nm, Lumex, part # SSL-LX5093SUVC. The photocatalyst could be a) mixed into the resin that is used to injection mold the chamber basin; b) mixed into the resin used for injection molding of the Handle or Head (of the Plunger or Brush); c) coated onto the inner surface of the chamber with a film—this is advantageous as "off the shelf" films may soon be available allowing for the film to be vacuum formed directly onto the inside surface of the unit's parts; d) a currently available solution is sprayed on in a solution and then dried to coat the entire inside of the unit (see e.g., GreenTekQuest.com); and/ or coating a high surface area textile like fiberglass cloth and then die-cut and shape the cloth to line the inside of the unit.

Use UV-C targeted to 253 nm with a glass CCFL Bulb. That this mode requires a) a non-LED bulb, and, b) more power than the unit described above. As demonstrated by VioLight and Steripen devices, this mode can still be powered by 4AA or 2 9V to provide more than 25 sanitization cycles. This mode also produces some Ozone that will kill some germs.

Use UV-C targeted to 253 nm with a special doped quartz CCFL Bulb. This mode is useful for variations of the device in which Ozone production is avoided.

Use UV-C targeted to 253 nm with a glass CCFL bulb and photocatalyst in the chamber. The UV-C provides a primary sterilization means while the photocatalytic oxidation provides as a secondary sterilization means, and Ozone serves as a tertiary sterilization. Again, while this may mode has drawbacks in size and production of Ozone, the effectiveness would be quite high and the cost would be medium.

Use UV-C targeted to 253 nm with a special doped quartz CCFL bulb and Photocatalyst in the chamber this would have UV-C as the primary method of sterilization and photocatalytic oxidation as the secondary. This mode avoids Ozone production. This mode requires a quartz CCFL bulb of a sufficient size to fit within the unit.

In each of the above modes, the photocatalyst could be provided in the plunger and/or base. Furthermore, the photocatalyst could be found in the actual housing. Alternatively or in combination, the photocatalyst could be inserted as a separate piece.

FIG. 8A also shows a variation of a plumbing tool 10 (e.g., a plunger) having an internal reservoir 14 that is reflectively coated to aid in UV light distribution. In addition, it is further noted that the unit may be used with plumbing tools comprising handles only (e.g., a tool without a plunger cup or brush such as a disposable head toilet brush provided by, for example, Clorox®, SC Johnson, or Scotch-Brite™).

FIG. 9A shows a cross sectional view of another variation of a unit 250 with a side view of a plumbing tool 12. As illustrated, the unit 250 includes a base 252, with a opening 260 for insertion of the plumbing tool. The unit 250 includes an illumination source 210 having associated circuitry 214 with a power supply 216. In this variation, the power supply 216 comprises a set of batteries placed within the unit. However, variations include power supplies that are external to the unit or plugs for AC power. The unit 250 also includes a reflective interior surface 262 (for example, the interior surface of the base 252 may be reflective, or an insert may be used).

FIG. 9A also shows a plumbing tool 12 in the form of a brush 12. The brush has a brush head or attachment 16 coupled to a shaft 18. The shaft includes a lid 20 that is receivable within or on the top of the unit 250 and a handle 22. As shown, the unit 250 may be provided with a standard plug 228 so that the UV source obtains power from a wall outlet.

As discussed herein, the unit 250 may also include a photocatalyst. For example, the photocatalyst may be provided in the material forming the parts of the unit (e.g., base, insert, lid, etc.) Alternatively, or in combination, the photocatalyst may be provided as a separate insert 230 that is placed within the unit (such inserts may also be combined with plungers and other plumbing tools as described herein.) In any case, the photocatalyst will be placed within a line-of-sight of the UV light source and/or it will be placed such that UV light shines onto and activates the catalyst.

FIG. 9B shows an exploded view of the unit 250. As shown, the unit may include the insert 262 within the base 252 and base cap 264 that is removable to access the electrical components and/or power supply. The bottom of the insert 262 is open or otherwise transparent to allow for the UV source (not shown) to deliver light into the insert 262. The insert 262 may also contain a cover 220 to help in preventing liquids from contacting the light source or associated components. FIG. 9B also shows a variation of the circuitry 214 and power supply 216 associated with the unit 250. In this variation, a switch 218 is used to trigger the light source. The switch 218 may limit the light source for activation upon placement of the tool. Alternatively, or in combination, the switch 218 may be a safety type switch that prevents or terminates the light source upon removal of the tool 12.

FIG. 9C illustrates a sectional view of a top portion of the unit 250. As shown, the switch 218 may be triggered by the weight of the tool or lid 20. Alternatively, the tool or lid 20 may complete the circuit of the switch 20 to trigger the UV cycle.

FIG. 9D illustrates a variation of the illumination source 210, circuitry 214, and power supply 216. In this variation, the circuitry 214 comprises a socket 222 for the UV source 210, the socket is coupled to a printed circuit board 224 for containing the algorithms or cycle information (see e.g., FIG. 10). In this variation, the circuitry 214 contains a starter 226, where the voltage regulator (not shown) is housed on the circuit board.

Examples of such parts may be found as follows: switch contact crimp-terminal A3B-A4B type (supplier Digi-Key part H9999-ND, manufacturer A3B-2630SCC); sensor wires 18-26 gauge; socket—#710 intermediate phenolic lampholder (supplier LightBulbDepot.com); lamp (9.09v, 2 watt, 0.22 amp, base—E17, shape T7, length 55 mm, UVC, supplier Bulbman.com); ballast (starter FS-5, manufacturer code 18344, supplier Bulbman.com).

FIG. 9E illustrates an exploded variation of a brush 12 for use with the present system. However, FIG. 9E illustrates features that may be incorporated with any plumbing tool as described herein. As shown, a plumbing tool may use a lid 20 member to activate the UV cycle and/or to block UV light. The lid 20 may be configured to permit a small amount of light to pass therethrough. This "escaped" light may be sufficient for the user to confirm activation of the UV light.

FIG. 10 illustrates a flowchart representation of a variation of the logic flowchart contained on a circuit board for controlling the unit.

The bases described herein may be provided in any suitable form. The base may be constructed to sealably hold the head of a plunger or toilet brush when not in use, typically with a portion of the plunger or brush (e.g., the handle portion) sticking up through an aperture in the top of the base, the base establishing a seal with the portion of the plunger or toilet brush that extends through the aperture.

In certain embodiments, the UV base is in the form of a clamshell having a bottom surface and two or more side panels or petals connected (e.g., as by hinges) to the bottom surface. The petals may be adapted to automatically close around the plunger or brush upon contacting the plunger or brush with the base.

Disposed within the interior of the base is an UV sterilization system including at least one UV light bulb or source. In many embodiments, a plurality of UV lights are provided and positioned about the interior of the base so as to be directed to different surface areas of the object being sanitized/sterilized.

In one embodiment, a first or bottom light source is positioned on the bottom surface of the base and adapted to sanitize or sterilize at least the bottom or underside of a toilet brush or plunger. In certain instances, top bristles of a brush or the top of a traditional plunger dome will not be exposed to light from this bottom-surface light source. Therefore, at least two additional UV bulbs or light sources may be included: one for each side of the top surface.

Embodiments may include a base having one or more top light sources positioned on one or more of the petals to sterilize the top or upperside and/or sides of a toilet brush or plunger. A light source may be associated with each petal of the base. For example, a 2-petal base may include 1 UV light source on the bottom and one UV light source on each petal for a total of 3 light sources, a 3-petal base may include 1 UV light source on the bottom and one UV light source on each petal for a total of 4 light sources, etc.

In certain embodiments, the light source(s) are automatically activated once a plunger or toilet brush is received for storage therein. After a predetermined period of time, the light sources may automatically turn off.

Also provided are kits that include the subject plunger devices. A kit may include a subject plunger device and one or more interchangeable liquid dispensing caps and brushes to be used with the plunger. In one embodiment, a kit may include a subject plunger device and a sterilization unit for sterilizing the device. The kit my further include instructions for use, various cleaning supplies, etc.

Devices and methods of the present invention include combinations of features/aspects of various embodiments as well as the combination of the embodiments themselves wherever possible. As for other details of the present invention, materials and manufacturing techniques may be employed as within the level of those with skill in the relevant art.

I claim:

1. A storage unit for sanitizing a plumbing tool, the unit comprising:
    a base adapted to sealingly hold the plumbing tool; and
    at least one UV light source within the base;
    wherein the base comprises at least one opening such that fluid within the base drains to a second portion within the storage unit allowing for the plumbing tool to be stored in a dry condition while sanitized.

2. The storage unit of claim 1, where the UV light source generates a wavelength of 253.7 nm.

3. The storage unit of claim 1, where the UV light source generates a plurality of wavelength from 100 nm to 400 nm in a single cycle.

4. The storage unit of claim 1, where the UV light source comprises UV-A or UV-C light.

5. The storage unit of claim 1, further comprising a photocatalyst.

6. The storage unit of claim 5, where the photocatalyst is placed in or on the base.

7. The storage unit of claim 1, wherein the base comprises a plurality of UV light sources.

8. The storage unit of claim 1, wherein the base comprises a bottom surface and a plurality of side panels.

9. The storage unit of claim 8, wherein the base comprises at least one UV light source and each of the side panels comprises at least one UV light source.

10. The storage unit of claim 1, where the UV light source provides light for a sufficient intensity and time to kill pathogens.

11. The storage unit of claim 1, where the UV light source is coupled to a timer that controls a cycle of the UV light source.

12. The storage unit of claim 1, further comprising a mirrored interior surface adapted to reflect UV light about the plumbing tool.

13. The storage unit of claim 12, further comprising an insert located within the base, where the insert comprises the mirrored interior surface.

14. The storage unit of claim 1, further comprising a switch electrically coupled to the UV light source.

15. The storage unit of claim 14, where the switch is triggered by the weight of the plumbing tool.

16. The storage unit of claim 1, further comprising a collar, where the collar is removably placed on the plumbing tool.

17. The storage unit of claim 1, further comprising a power supply electrically connectable to the UV light source.

18. The storage unit of claim 17, where the power supply comprises a AC power supply.

19. The storage unit of claim 17, where the power supply comprises a DC power supply.

20. The storage unit of claim 17, where the p DC power supply is located in or on the base.

21. The storage unit of claim 1, further comprising a fluid trap located at a bottom of the base.

22. The storage unit of claim 21, where the UV light source is also in optical communication with the fluid trap.

23. The storage unit of claim 1, further comprising a moveable gate, where when in an open position the moveable gate allows insertion of the plumbing tool into the base, and when in a closed position, the moveable gate prevents a substantial amount of UV light from exiting the base.

24. The storage unit of claim 1, further comprising the plumbing tool removably placed within the base.

25. The storage unit of claim 24, where a photocatalyst is located on the plumbing tool.

26. The storage unit of claim 25, where the photocatalyst is located within a material comprising the plumbing tool.

27. The storage unit of claim 24, where the plumbing tool comprises a tool selected from a group consisting of a plunger, a toilet brush, a toilet brush handle, and a plunger handle.

28. The storage unit of claim 24, where the plumbing tool further comprises a lid portion attached thereto, where the base top comprises an opening such that when the plumbing tool is placed within the base, the lid closes the base to prevent a substantial amount of UV light from exiting the base.

29. The storage unit of claim 24, where the plumbing tool comprises a plunger having an internal reservoir, where a surface of the reservoir comprises a reflective coating.

30. The storage unit of claim 24, where the plumbing tool comprises a plunger having an internal reservoir, where the internal reservoir comprises at least one secondary UV light source.

31. The storage unit of claim 24, where the plumbing tool comprises:
- a plunger body comprising an upper body portion and a lower body portion, where the upper body portion includes a handle and a gripping section;
- a reservoir located within the plunger body and terminating at an opening in the lower body portion, where the opening is adapted to direct fluid into the drain;
- a piston slidably moveable in the reservoir, such that movement of the piston displaces fluid from a first reservoir portion to a second reservoir portion, where the second reservoir portion comprises at least one port in the lower body portion allowing liquid in the second reservoir portion to exit the plunger body at a location away from the upper body portion; and
- a compliant member located adjacent to the opening, where the compliant member is sufficiently compliant to form a seal between the lower body portion and the drain allowing fluid to be drawn into the first reservoir portion via the opening.

32. The storage unit of claim 1, further comprising a UV light source in the second portion within the storage unit.

* * * * *